(12) United States Patent
Choulika et al.

(10) Patent No.: US 6,200,800 B1
(45) Date of Patent: Mar. 13, 2001

(54) NATURAL OR SYNTHETIC RETROELEMENT SEQUENCE ENABLING NUCLEOTIDE SEQUENCE INSERTION INTO A EUKARYOTIC CELL

(75) Inventors: André Choulika, Paris; Jean-François Nicolas, Noisy le Roi, both of (FR)

(73) Assignee: Institut Pasteur (FR)

( * ) Notice: Subject to any disclaimer, the term of this patent is extended or adjusted under 35 U.S.C. 154(b) by 0 days.

(21) Appl. No.: 09/000,227

(22) PCT Filed: Jul. 25, 1996

(86) PCT No.: PCT/FR96/01178

§ 371 Date: May 11, 1998

§ 102(e) Date: May 11, 1998

(87) PCT Pub. No.: WO97/06271

PCT Pub. Date: Feb. 20, 1997

(30) Foreign Application Priority Data

Aug. 7, 1995 (FR) .................................... 95 09587

(51) Int. Cl.[7] ........................... C12N 15/63; C12N 15/11; C07H 21/04; C12Q 1/68; C12P 21/06
(52) U.S. Cl. ...................... 435/320.1; 435/6; 435/69.1; 435/325; 435/375; 536/23.1; 536/23.5; 536/24.1; 514/44
(58) Field of Search .................. 435/5, 6, 69.1, 435/91.4, 456, 462, 325, 375, 320.1; 536/23.1, 23.72, 24.5

(56) References Cited

U.S. PATENT DOCUMENTS 5,629,159 * 5/1997 Anderson et al. ........................ 435/6

FOREIGN PATENT DOCUMENTS 0 300 422   1/1989  (EP) .
0 336 822  10/1989  (EP) .
WO 92/07943 10/1991 (EP) .
86/01178    7/1996  (EP) .

OTHER PUBLICATIONS

Orkin et al. Report and Recommendations of the Panel to Assess the NIH Investment in Research on Gene Therapy, 1995.*
Anderson. Human Gene Therapy. Nature. vol. 392. Supplement. pp. 25–30, Apr. 30, 1998.*
Verma et al. Gene Therapy—Promises, Problems and Prospects. Nature. vol. 389. pp. 239–242, Sep. 18, 1997.*
André Choulika et al., Transfer of Single Gene–Containing Long Terminal Repeats into the Genome of Mammalian Cells by a Retroviral Vector Carrying the cre Gene and the loxP Site, Nov. 28, 1995, vol. 70, No. 3, pp. pp. 1792–1798.

* cited by examiner

Primary Examiner—George C. Elliott
Assistant Examiner—Janet L. Epps
(74) Attorney, Agent, or Firm—Finnegan, Henderson, Farabow, Garrett & Dunner, L.L.P.

(57) ABSTRACT

Retroviral vectors contain cis-acting viral elements for the expression, encapsidation, reverse transcription and integration of the retroviral genome nucleic acid sequence. However, these elements are not useful in the integrated provirus and may cause many problems. A retroviral vector is provided for eliminating most of the viral elements. This vector uses, among other things, the bacteriophage P1 Cre-lox recombination system. The 32-nucleotide loxP site is inserted into 3'LTR sequence U3 with the gene to be inserted into the cell. After loxP duplication using the LTR, the LTRs may be recombined by enzyme Cre. The structure of the resulting provirus in the host genome corresponds to a single LTR carrying a single copy of the gene to be inserted into the cell. If the Cre expression unit is inserted between the two LTRS, only single-LTR proviral structures are found following infection with the retroviral vector.

22 Claims, 4 Drawing Sheets

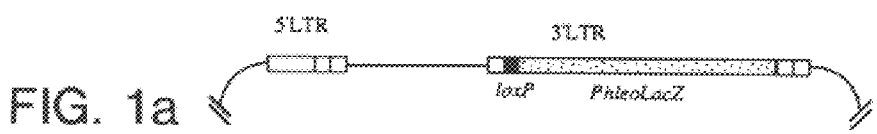
FIG. 1a
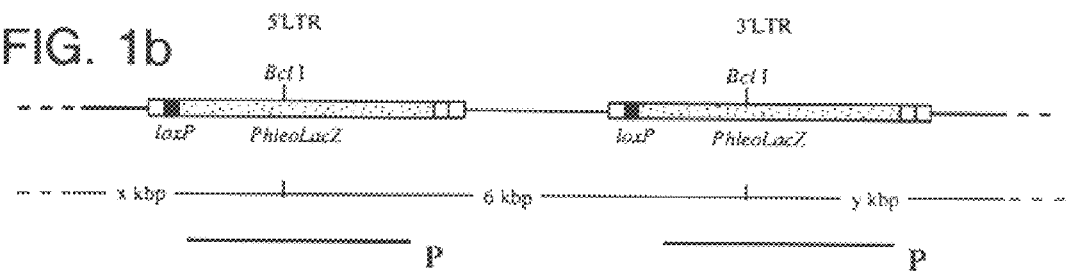
FIG. 1b
FIG. 1c
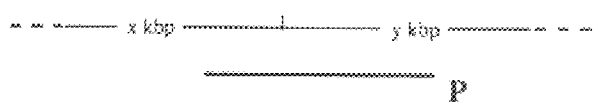
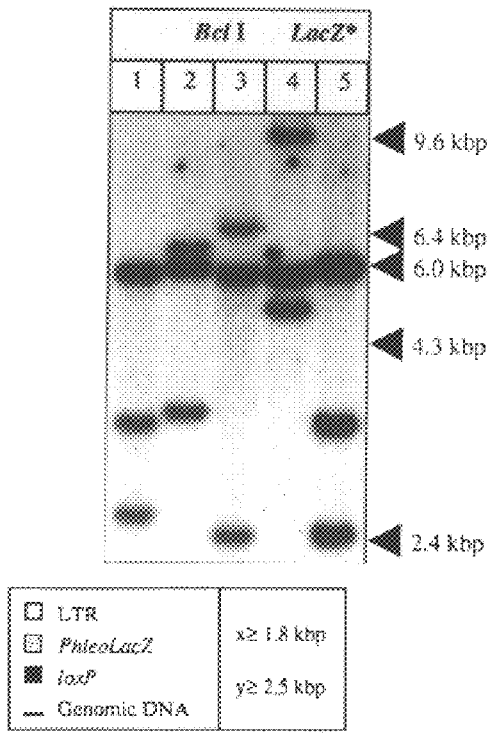
FIG. 1d
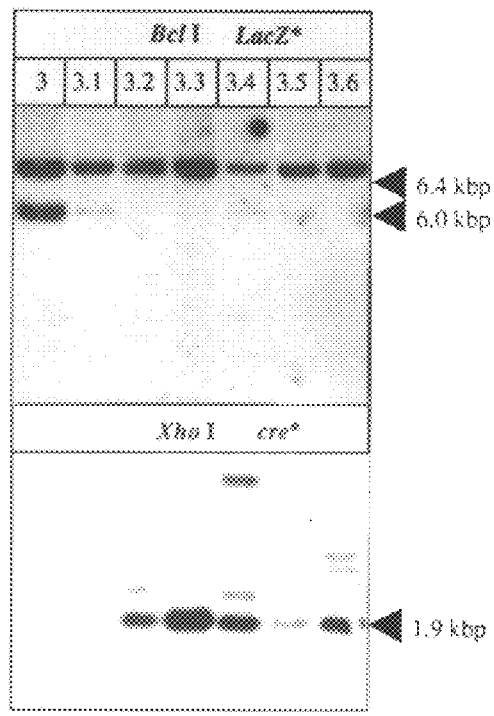
FIG. 1e

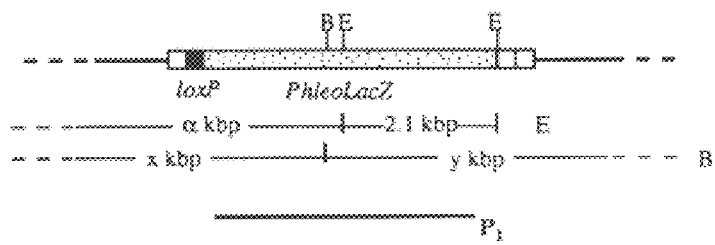
FIG. 2a
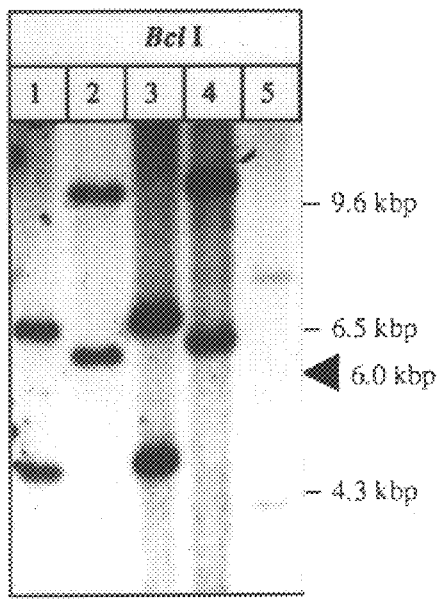
FIG. 2b
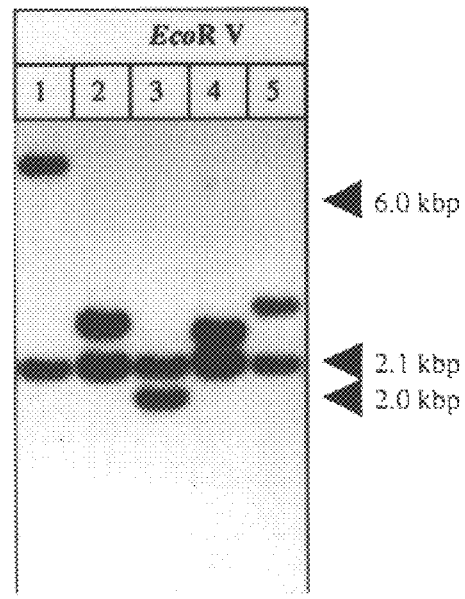
FIG. 2c
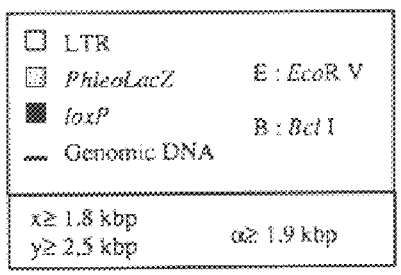

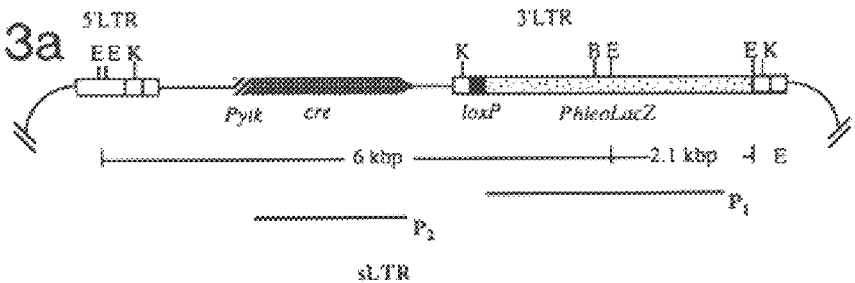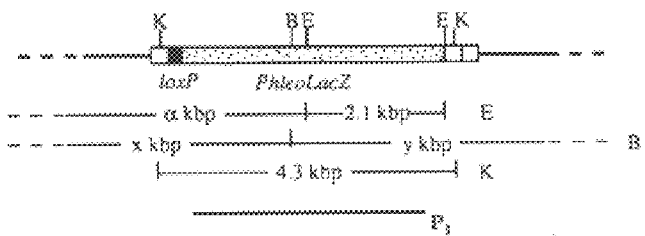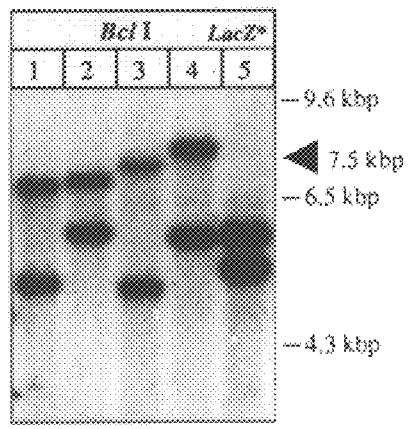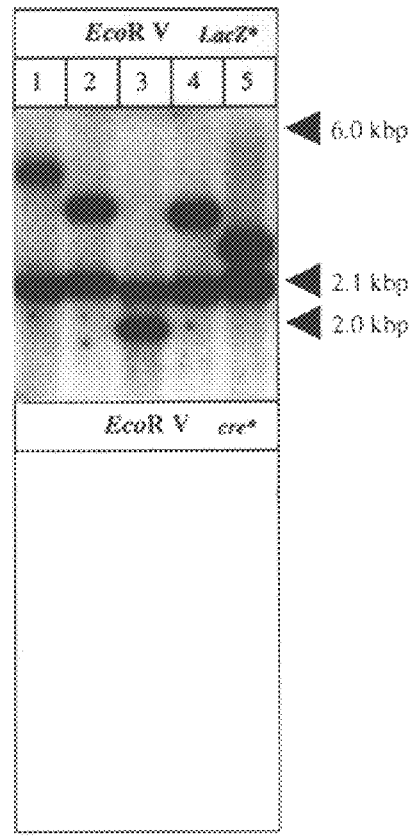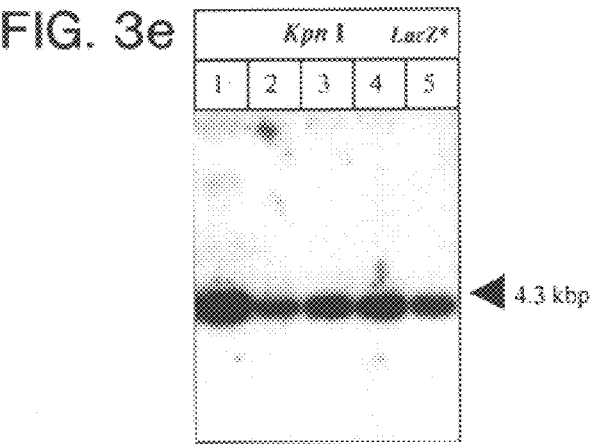

FIG. 4a
pMCreloxPL transfected into the ψ-2 transcomplementing cell line
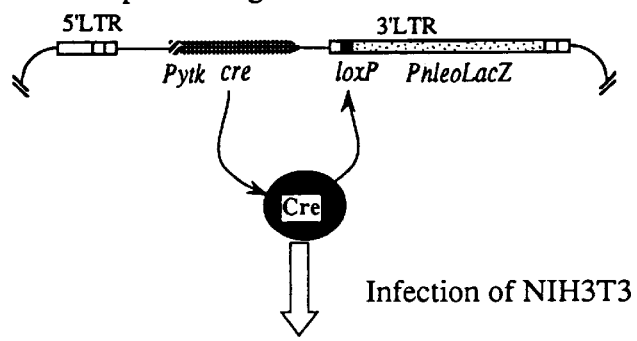
Infection of NIH3T3
FIG. 4b
MCreloxPL provirus integrated into the NIH3T3 cell line
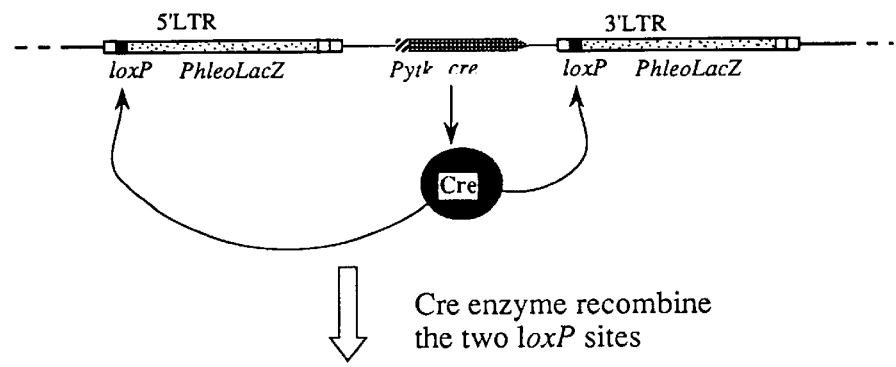
Cre enzyme recombine the two loxP sites
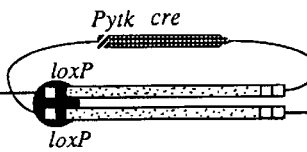
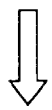
Recombination
FIG. 4d
The product of Cre-lox recombination is a sLTR
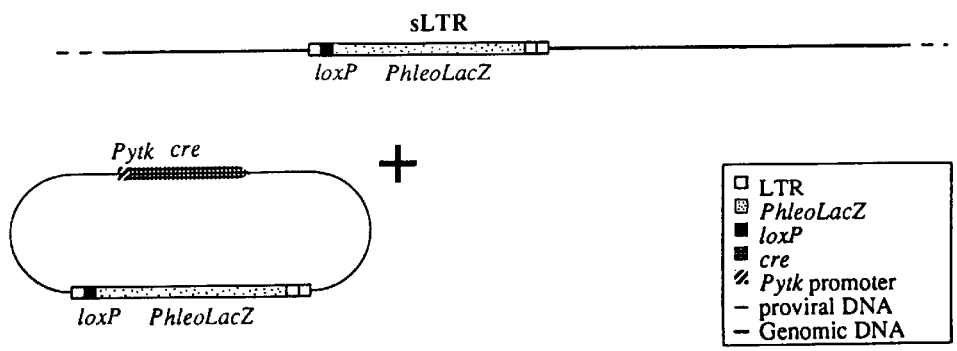
- □ LTR
- ▨ PhleoLacZ
- ■ loxP
- ▦ cre
- ▨ Pytk promoter
- — proviral DNA
- — Genomic DNA

```
                         SEQUENCE LISTING

<160> NUMBER OF SEQ ID NOS:   6

<210> SEQ ID NO 1
<211> LENGTH: 30
<212> TYPE: DNA
<213> ORGANISM: Artificial Sequence
<220> FEATURE:
<223> OTHER INFORMATION: Description of Artificial Sequence: primer

<400> SEQUENCE: 1
gcatcgagct gggtaataag cgttggcaat                                    30

<210> SEQ ID NO 2
<211> LENGTH: 29
<212> TYPE: DNA
<213> ORGANISM: Artificial Sequence
<220> FEATURE:
<223> OTHER INFORMATION: Description of Artificial Sequence: primer

<400> SEQUENCE: 2
gacaccagac caatggtaat ggtagcgac                                     29

<210> SEQ ID NO 3
<211> LENGTH: 29
<212> TYPE: DNA
<213> ORGANISM: Artificial Sequence
<220> FEATURE:
<223> OTHER INFORMATION: Description of Artificial Sequence: primer

<400> SEQUENCE: 3
```

-continued

```
ggactgggtg gcttccaact cccagacac                              29

<210> SEQ ID NO 4
<211> LENGTH: 30
<212> TYPE: DNA
<213> ORGANISM: Artificial Sequence
<220> FEATURE:
<223> OTHER INFORMATION: Description of Artificial Sequence: primer

<400> SEQUENCE: 4
agcttctcat tgctgcgcgc caggttcagg                             30

<210> SEQ ID NO 5
<211> LENGTH: 42
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 5
catgcatata acttcgtata gcatacatta tacgaagtta tc               42

<210> SEQ ID NO 6
<211> LENGTH: 42
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 6
catggataac ttcgtataat gtatgcttat cgaagttata tg               42
```

NATURAL OR SYNTHETIC RETROELEMENT SEQUENCE ENABLING NUCLEOTIDE SEQUENCE INSERTION INTO A EUKARYOTIC CELL

The present invention relates to a sequence of natural or synthetic retroelements, in particular an LTR retroviral nucleotide sequence, more particularly retroviral DNA as well as a retroviral vector containing this sequence and which enables, on infection of a cell into which it is desired to integrate a gene of interest contained in this vector, a large part of the proviral sequences which are no longer necessary after integration of the recombinant provirus to be eliminated.

Recent progress in the use of retroviruses as gene vectors falls into three classes: (i) improvement of the packaging cell lines, (ii) manipulation of the tropism of the envelope proteins, (iii) expression of multiple genes. The modification of the structure of the integrated provirus has not yet been very much exploited because this latter contains certain cis-acting essential elements. These elements are the source of many problems.

From the point of view of the structure, the retroviral vector system is constructed on two elements: the transcomplementing genes (gag, pol and env) and the cis-acting sequences (U3, R, U5, the polypurine track (PPT), the primer binding site (PBS) and the packaging and dimerization signal).

The transcomplementing genes are incorporated in transcomplementing cells. They are not transferred to the target cells.

The cis-acting sequences are incorporated into retroviral vectors. Most of them are transferred to the infected target cells and are integrated into the recombinant provirus. The elimination of any one of these cis-acting sequences results in a non-functional retroviral system. The packaging signal is necessary for the packaging of the retroviral genome in viral particles. PBS, PPT and R are required for reverse transcription. The U3 and U5 sequences are essential for reverse transcription and for the integration of the retroviral product introduced into the cell.

Once the provirus is integrated, these sequences are no longer necessary for the expression of the gene. On the contrary, these sequences may even cause many problems. (i) A transcriptional interference may result from the presence of the strong promoter in the U3 sequences. (ii) The PBS may function as a cis-acting inhibitory element for the internal promoters. For example, in the multipotent cells, the PBS is a recognition sequence for a strong repressor and in addition it acts as an inhibitory element. (iii) The U3 sequence contains at least one of the negative regulatory elements situated in the direct repeated activators at a distance between −345 and −306. (iv) The 3'LTR (long terminal repeat) can activate genes flanking cells with sometimes deleterious consequences for the cell. (v) The RNA expressed from the promoter of the 5'LTR contains the packaging signal and can, consequently, be recovered in a retroviral particle. This RNA can recombine with a cellular RNA or the retroviral RNA of a phenotype, resulting in the recovery of a retrovirus endowed with novel properties (creating a potential biological danger). These problems have not yet been entirely overcome since all these elements are necessary for the replication and the insertion of the virus into the genome.

In the context of the present invention, the inventors have developed a sequence of natural or synthetic retroelements, in particular a retroviral nucleotide sequence, and in particular a retroviral vector containing this sequence, designed so as to permit the elimination of a large part of the proviral sequences which are no longer necessary after integration of the provirus into a cell host. More particularly, this retroviral sequence is a retroviral DNA capable of permitting the integration of a single LTR sequence, a retrotransposon or a sequence comprising a U3, R or U5 region into the genome of a cell host.

The invention also relates to host cells, preferably eukaryotic cells, obtained after transfection by the retroelement sequence of the invention or a vector containing it.

The present invention hence concerns a retroelement sequence characterized in that it comprises an insertion sequence incorporated in a region capable of being transferred into a target cell and integrated into a recombinant provirus when this target cell is infected by a retrovirus containing this sequence. In particular, this insertion sequence is incorporated into a cis-acting region, more particularly in the 3'LTR or the 5'LTR region and preferably in the U3 region of the 3'LTR or the U5 region of the 5'LTR of this retroviral sequence. This insertion sequence comprises a nucleotide sequence of interest capable of being integrated into the genome of a cell host as well as a recognition sequence for a recombinase. Preferably, all of the retroviral sequence only contains a single recognition sequence situated with the sequence of interest, upstream or downstream for example, although this latter parameter is not absolutely necessary. The nucleotide sequence of interest may be situated downstream from the recognition sequence in as much as this latter is included in the region transferred into a target cell on infection of this target cell by a retrovirus containing the retroviral sequence. The maximal length of the insertion sequence that the retroviral vector of the invention contains is usually situated between 0.5 and 10 kb.

In particular, the sequence of the invention also comprises a DNA sequence coding for a recombinase capable of recognizing the sequence of its recognition site, this DNA sequence coding for a recombinase being advantageously situated between the 5'LTR and the 3'LTR regions of the vector. The invention also relates to a retroviral vector or recombinant retrovirus comprising the sequence described above. Preferably, the retroviral vector, which may take the form of a recombinant retrovirus, only contains a single recognition sequence incorporated into the region capable of being transferred to a target cell.

The DNA of the invention hence makes possible the insertion, through the intervention of a retroviral vector, of nucleotide sequences of interest in host cells, for example of the eukaryotic type, without the insertion of the proviral sequences which are no longer necessary after the integration of the sequences of interest in the provirus.

The term "nucleotide sequence of interest" used above refers to sequences to be inserted in the genome of host cells in order to allow these latter to produce molecules of interest, more particularly in therapy or for vaccination. These sequences of interest include, among others, genes, DNA or RNA sequences coding either for proteins (hormones, immunoglobulins, enzymes or others) when these retroviral vectors of the invention are used in gene therapy, or human or non-human proteins (such as viral proteins) when the retroviral vectors of the invention are to be used in the framework of vaccination protocols. The nucleotide sequences of interest may also be constituted in part of regulatory elements (i.e. promoter, enhancer) homologous or heterologous to the host cell on the one hand and, on the other hand, of sequences coding for all or part of one or more genes or complementary DNA. Furthermore, the nucleotide sequences of interest may also code for an antisense RNA or a ribozyme sequence.

The possible applications of the retroelement sequence of the present invention are manifold. The sequence of the invention is used either simply for the insertion of nucleotide sequences in host cells such as eukaryotic cells in an environment which promotes a better expression of this gene, or in gene therapy, or in vaccination. As an example, the sequence of interest described in Nature Medicine, Volume No. 7, July 1995 corresponding to the insert of the plasmids pMEPV$_H$/pMEPV$_L$ or pMEPV$_H$/pREPV$_K$ can be used and the in vivo expression product may be an element of a therapeutic composition.

The retroviral vector of the invention is obtained by the transfection of a transcomplementing viral cell line with a retroelement sequence of the invention existing preferably in the form of a plasmid and comprising preferably in one of its LTRs and more particularly in its right LTR a nucleotide sequence of interest as well as a recognition sequence. The plasmid may also contain a nucleotide sequence coding for a recombinase capable of recognizing the recognition site situated upstream or downstream from this sequence of interest, this nucleotide sequence being advantageously situated between the 3'LTR and 5'LTR regions. Once the transfection of the viral cell line has been performed, a retroviral vector is obtained which can be used for the infection of a cell host in which it is desired to integrate the nucleotide of interest.

The plasmid defined above as well as the method of transfection of the cell line by said plasmid are also included in the framework of the present invention.

The invention also relates to a method or procedure for the introduction of nucleotide sequences of interest into a cell host such as a eukaryotic cell. The method is characterized in that it comprises the introduction of a sequence corresponding to retroelements such as the U3, U5 and/or R regions into a eukaryotic cell, said sequence being linked to a nucleotide sequence of interest. This method is characterized by an infection step of a eukaryotic cell by a retroviral vector containing the retroviral sequence of the invention which contains the nucleotide sequence to be introduced into the eukaryotic cell under conditions permitting the integration into the cell genome of the cell of a single LTR of the retroviral vector containing the sequence to be introduced in the genome of the host cell and a second step of expression of the sequence of interest then the elements of the product of this latter starting from the recombinant cell.

The invention also relates to a method of medical treatment comprising the administration of an effective amount of a retroviral vector of the invention including a nucleotide sequence containing a gene capable of being integrated into the genome of certain target cells of the patient. The retroviral vectors of the present invention can thus be used in gene therapy.

The invention also relates to a cell host which has integrated into its genome a proviral structural containing a single LTR region of a retrovirus. This LTR sequence contains a single copy of a nucleotide sequence of interest. More particularly, the cell host of the invention is a eukaryotic cell and the proviral structure is characterized in that it is essentially free of the PBS sequence, the packaging and dimerization signal and/or the PPT signal.

The invention also relates to the recombinant cell hosts containing the unique LTR sequence or a part of this latter and the sequence of interest.

The invention also relates to the use of the retroelement sequence or the retroviral vector of the invention in the production in host cells of proteins encoded in a nucleotide sequence of interest included in this retroviral DNA or in the medical treatment of a patient for the purpose of integrating a nucleotide sequence of interest in the genome of target cells.

More particularly, the sequence of the invention also makes possible the transfer of nucleotide sequences coding for antibodies into host cells. One speaks of extracellular immunization since the antibodies generated from these sequences produce their effect within the cells which have integrated them. Among the nucleotide sequences coding for antibodies which can be integrated into host cells by using the retroviral sequence and the retroviral vector of the invention, mention may be made as non-limiting examples of the antibodies recognizing envelope proteins of the HIV viruses, particularly the gp 120 proteins of the HIV-1 virus and the HIV-2 virus as well as antibodies making it possible to block the reverse transcriptase. Such antibodies are described in the publication by Maciejewski et al. (Nature Medicine, volume No.7, July 1995) and elsewhere. Since the retroviral vector of the invention makes possible a more efficacious integration of these nucleotide sequences of interest, the therapeutic efficacy of this approach is all the more improved.

The invention hence relates to the use of retroviral vectors comprising a nucleotide sequence of interest coding for an antibody recognizing a HIV viral protein or protein fragment, as well as a recognition nucleotide sequence, these two nucleotide sequences being situated in a region which can be transferred into human lymphocytes subsequent to an infection. Preferably, these two sequences are situated in the 3' LTR region of the retroviral vector.

The invention also relates to an expression method or procedure for a molecule encoded by a nucleotide sequence of interest in a host cell. The method comprises:

the infection of the host cell by a retroviral vector of the invention containing the nucleotide sequence of interest;

the growth of the host cell under conditions permitting the expression of the nucleotide sequence of interest; and the production of the desired molecule.

The retroviral nucleotide sequence as well as the retroviral vectors of the invention can be used in several ways to enable the desired nucleotide sequence of interest to be integrated. In fact, the inventors have demonstrated that it was not necessary to associate the expression of the recombinase directly with the retroviral vector, although the integration yields are higher when a nucleotide sequence coding for the recombinase is an integral part of the vector.

In a first embodiment of the invention, a retroviral vector containing in the 3' LTR or the 5' LTR region of the retroviral vector a first nucleotide sequence comprising a nucleotide sequence of interest as well as a recognition sequence situated downstream or upstream from the sequence of interest, as well as a second nucleotide sequence identical with the first nucleotide sequence inserted in the 5' LTR region of the vector, is introduced into the genome of a host cell by infection. A plasmid comprising a nucleotide sequence coding for a recombinase capable of recognizing the recognition sequence is also introduced into the cell by transfection. The expression of the recombinase by transfection transforms the structure of a provirus with two LTRs into a provirus with a single LTR. In this type of reaction, about 50% of the stable transformants contain the modified provirus. This partial result may be explained by the ephemeral expression of the plasmid comprising the nucleotide sequence coding for the recombinase after the transfection, resulting in recombination without integration.

In a second embodiment of the invention, use is made of a retroviral sequence containing a nucleotide sequence containing a sequence of interest as well as a recognition sequence situated downstream or upstream from this sequence of interest. The complete sequence is inserted in the 3' LTR region of a retrovirus. The retroviral vector thus obtained is then used to infect a cell line which expresses constitutively or by induction a recombinase capable of recognizing the recognition sequence. The efficacy of such a system is high, especially when the gene coding for the recombinase is expressed right from the start of the retroviral infection.

In a third embodiment of the invention, a retroviral vector comprises a nucleotide sequence inserted into its 3' LTR region. This nucleotide sequence contains a sequence of interest as well as a recognition sequence which can be recognized by a recombinase. The recognition sequence is situated downstream or upstream from the sequence of interest. Furthermore, a gene coding for a recombinase as well as a promoter are integrated into the retroviral vector between the two LTRs of this vector. A cell line is then infected with this retrovirus. Such a retroviral vector only generates proviruses with a single LTR. The efficacy of this system is high since all of the integrated and analyzed events have this structure. The principal advantage of such a retroviral vector is that it is associated with successful recombination events between the two LTR with the deletion of the gene coding for the recombinase. Consequently, the infected cells only express the recombinase ephemerally.

In one of the preferred embodiments of the invention, the inventors used the Crelox recombinase system specific for the site of the bacteriophage P1. The recognition site LoxP was inserted into the 3' LTR upstream from the nucleotide sequence of interest in a ΔEnh type vector, and the gene coding for the recombinase cre between the two LTRs. In the producing cell line, the Cre protein is expressed from the proviral plasmid construction. However, since the plasmid only contains a single target loxP, it is not recombined by the Cre protein. After infection, the loxP site is duplicated from the 3' LTR into the 5' LTR. Thus, Cre recombines the two direct repeated loxP sites, which results in the deletion of all the sequences included between the two loxP, including the PBS, the dimerization and encapsidation signal and the PPT. Thus only a single LTR containing the reporter gene remains integrated in the cell genome. The cre gene is also lost during recombination.

In all the preferred embodiments described above, the nucleotide sequence of interest, which is generally a sequence foreign to the retrovirus, is advantageously introduced into the U3 region of 3' LTR of the retroviral sequence. In fact, the possibility of introducing sequences, even complete transcriptional units, into the U3 region of 3' LTR is very well documented. Nonetheless it is possible to envisage the introduction of sequences of interest elsewhere than in the U3 region of the 3' LTR of the retroviral vector. Examples include the U5 region of the 5' LTR. Furthermore, although it is preferable that the recognition site is situated immediately downstream or upstream from the nucleotide sequence of interest, it is also possible to place this sequence at an appreciable distance which may vary between 32 nt and 4.5 kb without affecting the final integration of the sequence of interest into the target cell.

The quantity of foreign genetic material introduced into the U3 region of the viral DNA may be high and in some cases higher than 4 kbp. These sequences may even correspond to a complete transcriptional unit with an independent promoter, which demonstrates the versatility of these vectors.

The possibility of introducing considerable quantities of foreign genetic material into the 3' LTR of the retroviral vector of the invention makes this retroviral vector a system of choice for the insertion of gene sequences into cells, more particularly into eukaryotic cells. Several types of eukaryotic cells can thus be transformed. Of the eukaryotic cells which may be used in the context of the present invention, particular mention should be made of the following types of cells: NIH 3T3, BRL, HM1, D3, PLL4, LT.

In one of the particular embodiments of the present invention, provision is made for the insertion of a nucleotide sequence coding for a marker in the 3' LTR region of the retroviral vector. The presence of this marker makes it possible to prove the insertion of the new product.

As non-limiting examples, the following markers may be used: LacZ, GFP (green fluorescent protein), CD9, PAL (alkaline phosphatase) and HRP (Horse Radish Peroxidase).

Although the Crelox recombinase system constitutes a system of choice for the retroviral vector of the invention, other recombinase systems can also be used. As non-limiting examples, the following recombination systems may be used: the yeast FLP system (called "Flip") and the bacterial R system.

The retroviral vectors of the invention hence furnish an efficient agent for the transfer of DNA into host cells. The proviral integration is precise and does not cause chromosomal rearrangement. The design of duplicating vectors set out from the principle that the transposition of the gene into the 5' LTR, outside the retroviral transcriptional unit, improves its expression.

Although the presence of the encapsidation signal makes possible the generation of a virus competent for replication by recombination between the endogenous sequences of the retrovirus and the provirus, that the presence of PPT and other cis-elements make transposition possible and that the presence of the PBS sequences may have negative effects on the expression of the transgene, all these events are very improbable when a retroviral vector according to the invention is used since all these viral sequences are deleted.

The system of the LTRs is a novel concept in the construction of retroelements in general. There are many retroviruses, the host spectrum of the particle of which is of interest but for which the design of vectors requires the presence of certain cis- or trans-acting sequences different from those which have been mentioned previously which make possible a correct assembly of the virion and enable it to be infectious, like for example the human HIV and HTLV viruses or the goat virus CAEV. Once integrated, the cis or trans regulating elements become useless for the transduced gene but have pathogenic effects for the cell and significantly increase the probabilities of the resurgence of the wildtype virus. The necessity of this type of sequence for this type of retrovirus makes them practically unusable for employment as vectors. The application of the LTRs system of the present invention in the case of these retroviruses makes it possible to envisage a usage as vectors for the transduction of genes with more transcriptional safety and fidelity.

The present invention should be clearly described with reference to the following non-limiting examples which make reference to the following figures:

FIG. 1*a* presents the structure of the plasmid pMloxPL;

FIG. 1*b* presents the structure of the provirus MloxPL resulting from the infection with the retrovirus MloxPL;

FIG. 1*c* presents a provirus after the recombination induced by cre using the two loxP sites within the LTRs;

FIG. 1*d* presents an analysis by "Southern blot" of the cellular DNA derived from NIH3T3 fibroblasts infected by MloxPL;

FIG. 1e presents an analysis by "Southern blot" of the cellular DNA derived from the clone NIH3T3 MloxPL.1 transfected by the plasmid pMC1-Cre;

FIG. 2a presents the structure and molecular analysis of the provirus MloxPL resulting from the infection with the retrovirus MloxPL and the recombination induced by Cre using the two loxP sites within the LTRs;

FIG. 2b presents the results of an analysis by "Southern blot" of the cellular DNA derived from NIH 3T3 Cre.1 fibroblasts infected by MloxPL with digestion by the restriction endonuclease BclI;

FIG. 2c presents the results of an analysis by "Southern blot" of the cellular DNA derived from NIH 3T3 Cre.1 fibroblasts infected by MloxPL with digestion by the restriction endonuclease EcoRV;

FIG. 3a presents the structure of the plasmid pMCreloxPL;

FIG. 3b presents a diagram of the 3' LTR of several preferred embodiments of the retroviral vector of the invention;

FIG. 3c presents the results of an analysis by "Southern blot" of the cellular DNA derived from NIH 3T3 fibroblasts infected by MCreloxPL by digestion by the restriction endonuclease BclI;

FIG. 3d. presents the results of an analysis by "Southern blot" of the cellular DNA derived from NIH 3T3 fibroblasts infected by MCreloxPL by digestion by the restriction endonuclease EcoRV;

FIG. 3e presents the results of an analysis by "Southern blot" of the cellular DNA derived from NIH 3T3 fibroblasts infected by MCreloxPL by digestion by the restriction endonuclease KpnI;

FIGS. 4a–4d presents a scheme for the mechanism of the generation of LTRs with the retroviral vector McreloxPL.

EXAMPLES

Nomenclature

The nomenclature of the various vectors and different cells was established as follows: p designates the plasmid vector (for example, pMloxPL); the names with a ψ2 (deposited on Oct. 3, 1993 with the ECAC under the number 93031002) designate the cell line of the wildtype helper virus ψ2 transfected with this vector (for example, ψ2-MloxPL) ; the names without p designate the viruses produced by the cells of the wildtype helper virus (for example, MloxPL); the name of the cell line followed by the name of the virus indicates that the cell line contains a provirus resulting from an infection (for example, NIH 3T3MloxPL).

Culture and Selection of the Cells

The established cell lines NIH3T3 (mouse fibroblasts) and ψ2 (encapsidation cell line of the mouse ecotropic retrovirus) are referenced in (7) and (13). They are cultured in a DMEM (Eagle medium modified by Dulbecco) with a high glucose content (4.5 g/l) supplemented with 5% fetal calf serum. The cells are incubated at 37° C. in a moist atmosphere containing 12% of $CO_2$. G418 is added to the appropriate medium at a concentration of 600 mg/ml. The cloning of colonies resistant to G418 was done by pipetting individual colonies and isolating them in a separate culture dish. The cloning of the infected cells is performed by limiting dilution 48 hours after the infection.
Transfection, infection, staining of the cells and analysis of the nucleic acids by "Southern blot"
Precipitations by means of calcium phosphate were performed as described in (12). The supernatant containing the virus was used to infect NIH 3T3 cells in the presence of 5 μg/ml of polybrene, as previously described in (37). Hybridizations by "Southern blot" were prepared by means of the procedure in reference (6). The β-galactosidase activity was detected by staining with X-gal, as previously described in (38).

Detection of LacZ by PCR

The PCR is performed on 1 μg of genomic cellular DNA in a reaction of 40 μl (50 mM Tris-HCl (pH9), 150 μg/ml of bovine serum albumin, 16 mM $(NH_4)_2SO_4$, 7 mM $MgCl_2$, 250 μM for each dNTP, 1.25 U Taq DNApol (USB), 0.078 U Vent(exo$^+$) DNApol (N.E. Biolabs)). Primers were added at a final concentration of 0.25 μM (for 20 mers). The PCR was heated at 80° C. for 5 minutes before the start. 35 cycles (94° C., 55 min.; 59° C., 30 s; 70° C, 3 min. 30 s) with the following primers: 5'-GCATCGAGCTGGGTAATAAGCGTTGGCAAT -3' (SEQ ID NO:1) and 5'-GACACCAGACCAATGGTAATGGTAGCGAC-3' (SEQ ID NO:2) for the detection of LacZ and 5'-GGACTGGGTGGCTTCCAACTCCCAGACAC -3' (SEQ ID NO:3) and 5'- AGCTTCTCATTGCTGCGCGC-CAGGTTCAGG -3' (SEQ ID NO:4) for the detection of the endogenous RAP-SYN of mouse, as internal standard. The reaction products of the PCR were analyzed by gel electrophoresis.

Example 1

Construction of the Retroviral Vector pMloxPL and Transfection of Cell Lines a) Construction of the vector pMloxPL pMloxPL results from the plasmid (described in Choulika et al., 1995) in which the loxP recognition site is inserted within the Nco I site in a linker (5' CATGCATATAACTTCGTATAGCATACATTATACGAAGTTATC-3' (SEQ ID NO:5) and 5'- CATGGATAACTTCGTATAAT-GTATGCTTATCGAAGTTATATG - 3' (SEQ ID NO:6) in place of the I-Sce I site. The sequence of the loxP site was verified by sequencing of the DNA.

The retrovirus used is illustrated in FIG. 1a. pMloxPL is constructed from a defective Moloney murine leukemia provirus (lacking the gag, pol, and env genes) by inserting the sequence coding for PhleoLacZ in the U3 region of the right LTR in the place of the activation sequences at a distance. 5' derived from the PhleoLacZ gene was placed between the splicing acceptor site of the env gene of MoMuLV and a 32 bp long loxP site derived from the bacteriophage P1. In the infected cells this type of virus has the LTR which contains the gene enhanced by a flanking cell promoter by trapping of the promoter.

b) Transfection of cell lines with the plasmid pMloxPL

The cell lines producing the virus were generated by transfecting the plasmid pMloxPL with the selection plasmid pUSVneo in the cell line of the wildtype helper virus ψ2 which expresses the ecotropic wildtype helper virus defective for encapsidation. After selection for G418 (neomycin), individual clones selected for their β-galactosidase activity were tested to titer the virus. The titration was performed by cloning NIH3T3 cells immediately after infection by limiting dilution, and by detecting the presence of the provirus containing LacZ by PCR. The cell lines producing ψ2-MloxPL.1 and ψ2-MloxPL.2 showed a titer on the NIH 3T3 cell line of $2.5 \times 10^4$ and $5 \times 10^4$ (Table 1), respectively. The titration of the units forming blue colonies per milliliter (BCFU/ml) of the viral supernatant of ψ2-MloxPL.1 and ψ2-MloxPL.2 is 3 and 6, respectively, which corresponds to an approximate ratio of 1 blue colony per $10^4$ integrations. As we have previously described, these proviruses function as promoter traps, and only one integration out of $10^4$ expresses the reporter gene in the NIH3T3 fibroblast cell line.

The structures of the DNA of the integrated MloxPL proviruses are schematized in FIG. 1b. In the Figures to the present text, the positions of the LTRs and of the BclI restriction sites and the sizes of the fragments are indicated (x indicates the BclI fragment of random size of the left arm and y the BclI fragment of random size of the right arm. P indicates a LacZ probe radiolabelled with $^{32}$p. These structures were then analyzed by means of hybridization by "Southern blot" in 6 independent NIH 3T3 clones. The results of this analysis are presented in FIG. 1d. All of the clones contain a provirus in which the sequences within the U3 region of the 3' LTR have been duplicated in the 5' LTR; the digestion by the endonuclease BclI generates the expected fragment from the part of the proviruses with two LTR containing PhleoLacZ (the restriction enzyme BclI has a recognition site in each LacZ sequence in the LTRs). The hybridization by "Southern blot" using lacZ as probe, shows a 6 kbp cleavage fragment demonstrating a faithful duplication of the U3 region. The two additional bands of variable sizes represent fragments which extended from the BclI sites in the provirus to the flanking cellular DNA. The two additional bands show that there is one proviral integration per clone, and their variable sizes confirm that each cell line was an independent clone.

Example 2

Cotransfection of Cell Lines with the Plasmids pMloxPL and pMCl-Cre

We have examined whether the loxP duplication through the intermediary of the LTR may be recombined by the Cre recombinase. We have used the clonal cell line NIH3T3 MloxPL.1 to target a recombination with the Cre protein. We have cotransfected into this cell line the expression vector pMCl-Cre with the selection vector pUSVneo. The structure of the provirus after the recombination induced by Cre is illustrated in FIG. 1c.

The DNA of 24 clones resistant to neomycin was analyzed by means of hybridization by "Southern blot". The detection of the recombined proviruses was performed by analyzing the BclI digestions. The restricted DNA of the clones was probed with a LacZ radiolabelled with 32p. The results of this analysis are illustrated in FIG. 1e. The parental structure of the provirus shows a 6 kbp band corresponding to the faithful duplication of the U3 sequence containing LacZ and two additional bands of 8 and 2 kbp (described above (FIGS. 1b & d)). The analysis of the DNA of the clones resistant to neomycin shows 5 clones out of 24 in which the 6.0 kbp band has been eliminated (FIG. 1e). The bands of 8 and 2 kbp corresponding to the cell DNA flanking the provirus were still present, thus showing that the proviral integration site has not been rearranged. This result suggests that the expression of the cre gene in a cell containing the MloxPL provirus may lead to a frequent recombination of the two loxP sites included in the LTR.

In order to test the efficiency of the recombination through the intermediary of Crelox, we have also analyzed the DNA of 25 clones resistant to G418 by means of hybridization by "Southern blot" in order to test the presence of the cre sequence. The DNA was digested with the restriction endonuclease XhoI and probed with a full length cre DNA radiolabelled with $^{32}$p The results of this analysis are illustrated in FIG. 1e. Three of the five clones recombined in loxP show a band hybridizing with the 1.9 kbp cre probe suggesting that the full length cre expression unit of pMCl-Cre is present. One of the five clones recombined in loxP did not show a band hybridizing with the cre probe. One clone recombined in loxp shows a 5 kbp band resulting from a rearrangement of the pMCl-Cre plasmid. Four other clones showing a 1.9 kbp band hybridizing with cre do not show recombination in the integrated provirus MloxPL. We have not detected the presence of cre DNA in the remaining 16 clones. This result shows that the efficacy of the recombination induced by the presence of the pMCl-Cre is not absolute in the stable transfected cell lines, where only 50% of the loxP sites are recombined. This result also suggests that the recombination between the two loxP sites may be obtained through the ephemeral expression of pMCl-Cre (Table 2).

Example 3

Infection of the Cells Expressing the Cre Enzyme with MloxPL

We have produced an NIH3T3 cell line containing the pMCl-Cre by cotransfection of the plasmids pMCl-Cre and pUSVneo. Clones were selected in a medium containing G418 and their DNA was analyzed after digestion with the restriction endonuclease XhoI by means of hybridization by "Southern blot". The presence of the Cre gene was detected by hybridization with a full length cre DNA probe radiolabelled with $^{32}$p. Ten of the 12 clones resistant to G418 analyzed revealed the presence of the Cre sequence in a variable number of copies (ranging approximately from 1 to 10 copies) (data not shown).

We chose the clone NIH3T3Cre.1 containing approximately 10 copies of the pMCl-Cre plasmid for the purpose of supplementary analysis. We infected the clone NIH3T3Cre.1 with the MloxPL virus. The clones were isolated by limiting dilution.

The structure of the provirus resulting from the infection of the MloxPL retrovirus and the recombination induced by Cre is illustrated in FIG. 2a. The structure of the integrated vector is a solitary LTR (sLTR). It lacks an LTR and all of the sequences situated between the two LTRs in the integrated proviruses (FIGS. 2a & c).

The structure of the DNA of the MloxPL proviruses was analyzed by means of hybridization by "Southern blot" after digestion by the restriction endonuclease BclI of their cell DNA in order to detect the presence or absence of duplicated LTR in the proviral structure. As demonstrated in FIG. 2b, the analysis of the 12 clones resulting from the infection of NIH3T3Cre.1 by MloxPL showed the absence from all of the clones of the 6 kbp band indicative of the duplication.

In order to demonstrate the absence of the 5' LTR from the provirus, a restriction of the DNA was performed with EcoRV. The hybridization by "Southern blot" of the DNA of NIH3T3Cre.1.MloxPL, restricted by the endonuclease EcoRV by using a radiolabelled LacZ probe (FIGS. 2a & c), shows the presence of a 2.1 kbp band and a band of random size. The absence of a 3.9 kbp band demonstrates the absence of a 5' LTR.

Example 4

Construction of the Retroviral Vector pMcreloxPL and Transfection of Cell Lines a) Construction of the pMcreloxPL plasmid The structure of the retrovirus used in the present example is illustrated in FIG. 3a. pMCreloxPL results from the insertion of the 1.3 kbp cre gene fused with a nuclear localization of the large T antigen of the simian virus 40 between the two LTR of the pMloxPL plasmid. The cre gene is under the transcriptional control of the promoter of the thymidine kinase gene (tk) of the herpes simplex virus flanked by a duplication of the enhancer at a distance of the polyoma mutant virus PYF441 with linkers at the PstI site of pMloxPL. The Cre sequence is in the same orientation as the viral genome. The pMcreloxPL plasmid was deposited with the CNCM on Jun. 13, 1995 under No.I-1599.

b) Transfection of cell lines with the plasmid pMcreloxPL

Cell lines producing the virus were generated by cotransfecting the pMCreloxPL plasmid with the selection plasmid pUSVneo into the encapsidation cell line $\psi 2$. After selection of the transfected $\psi 2$ cells in a medium containing G418, individual clones were selected for the production of a retrovirus expressing LacZ. One clone produced an infectious virus; this clone was called $\psi 2$-MCreloxPL.1. In $\psi 2$-MCreloxPL.1, the pMCreloxPL plasmid was integrated as a single copy into the host cell genome (data not shown). The cell lines producing $\psi 2$-MCreloxPL.1 produce $1 \times 10^4$ infectious viruses per milliliter; the presence of the LacZ gene is detected by PCR (Table 1). The titration of the blue colony forming units (BCFU/ml) of the $\psi 2$-MCreloxPL.1 viral supernatant is 3 BCFU/ml, which corresponds as expected to a approximate diminution of $10^4$ with respect to the titration by PCR. The production of $\psi 2$-MCreloxPL was of low efficiency compared with the production of $\psi 2$-MloxPL, a single producing clone having been recovered after several cotransfection experiments. This clone had integrated a single copy of the viral plasmid construction. We deduced from this that the cells which integrate more than one copy of the plasmid cannot be recovered owing to the presence of the recombinase activity which modified the integrated transgenes.

c) Proviral structure of MCreloxPL

The isolation of NIH3T3 cells infected with MCreloxPL was performed by limiting dilution, after infection at a multiplicity of 0.5 viral particle per cell. The structure of the provirus resulting from the infection of the retrovirus pMCreloxPL is illustrated in FIG. 3b. In this figure, $\alpha$ indicates the random size fragment of the left arm.

The structure of the DNA of the integrated proviruses was analyzed by means of hybridization by "Southern blot" in 6 independent NIH3T3MCreloxPL clones. The analysis by "Southern blot" of the proviral DNA restricted by the BclI endonucleases and detected with a radiolabelled LacZ probe generated two fragments of variable sizes, and these clones did not generate an additional 7.5 kbp band (FIG. 3c). The absence of this additional 7.5 kbp fragment demonstrates the presence of a single LTR containing PhleoLacZ. In order to establish in addition that the proviral structure corresponds to a single LTR, an additional analysis was undertaken. In order to demonstrate definitively the absence of a 5' LTR in the provirus, a restriction by EcoRV of the cellular DNA was performed. The hybridization by "Southern blot" of the DNA of NIH3T3MCreloxPL, restricted by the endonuclease EcoRV by using a radiolabelled LacZ probe (FIG. 3d) shows the presence of a 2.1 kbp band and a band of random size. The absence of a 6 kbp band demonstrates the absence of a 5' LTR. This "blot" was then hybridized with a radiolabelled cre probe. The absence of a band in the DNA of NIH3T3MCreloxPL shows that the proviral DNA lacked the cre gene (FIG. 3d). Finally, in order to establish that the structure of the remaining LTR had not rearranged, the DNA of NIH3T3MCreloxPL was restricted by the endonuclease KpnI and probed with a DNA of radiolabelled LacZ. A 4.3 kbp fragment was observed in all cases, showing that the LTRPhleoLacZ was of the expected size (FIG. 3e).Consequently, all of the isolated clones contained an integrated provirus with a single unrearranged LTR.

TABLE 1

Titers of the cell lines $\psi$ 2-MloxPL and MCreloxPLa

| Clone | IP/ml[b] ($10^4$) | BCF/ml[c] | Ratio[d] ($10^{-4}$) |
|---|---|---|---|
| $\psi$2-MloxPL.1 | 2.5 | 3 | 1.2 |
| $\psi$2-MloxPL.2 | 5 | 6 | 1.2 |
| $\psi$2-MCreloxPL.1 | 1 | 3 | 3 |

[a]Clones resistant to G418 derived from the clone NIH3T3MloxPL.1 cotransfected with pMC1-Cre and pUSVneo
[b]indicates the presence of the pMC1-Cre sequence
(+) indicates the presence of a correct 1.9 kbp XhoI fragment derived from pMC1-Cre detected by a cre probe labelled with $^{32}$P.
(*) indicates the presence of a XhoI fragment hybridizing with the $^{32}$P radiolabelled cre probe, but of incorrect size.
(-) indicates the absence of the pMC1-Cre plasmid.
[c]Results of the loxP recombination through the intermediary of Cre detected by means of "Southern blot" analysis.

TABLE 2 loxP Recombination through the intermediary of a pMC1-Cre transfection

| Number of clones resistant to G418[a] | Presence of pMC1-Cre[b] | loxP[c] recombination |
|---|---|---|
| 3 | + | + |
| 1 | – | + |
| 1 | * | + |
| 4 | + | – |
| 16 | – | – |

[a]$\psi$2 cells were transfected respectively with either pMloxPL + pUSVneo or pMCREloxPL + pUSVneo, clones resistant to G418 were selected in a medium containing G418. Stocks of virus were prepared by incubating 8 ml of medium with $5 \times 10^6$ cells of each clone resistant to G418, $5 \times 10^4$ NIH3T3 cells were subjected to various dilutions of the virus for 8 hours and then cloned by limiting dilution or tested for their β-galactosidase activity by staining with X-gal.
[b]The titers were calculated by the ratio between the infected clones isolated after cloning and detected by PCR (IP: infectious particle) and the uninfected clones (PCR+/PCR–)/$1 \times 10^5$)
[c]BCFU is the acronym for "blue colony forming unit". The BCFU are infections resulting in a trapping of the gene which activates the PhleoLacZ detected by staining with X-gal.
[d]The ratio is the number of BCFU per infected clone.

References

1. Barker, D. D., H. Wu, S. Hartung, M. Breindl, and R. Jaenisch. 1991. Retrovirus-induced insertional mutagenesis: mechanism of collagen mutation in Mov13 mice. Mol. Cel. Biol. 11:5154–5163.

2. Choi, S. Y., and D. V. Faller. 1994. The long terminal repeats of a murine retrovirus encode a trans-activator for cellular genes. J. Biol. Chem. 269:19691–19694.

3. Choulika, A., A. Perrin, B. Dujon, and J. F. Nicolas. 1994. Site-specific induction of homologous recombination in mammalian cells by I-Sce I system of Saccharomyces cerevisiae. Submitted to Science 4. Choulika, A., A. Perrin, B. Dujon, and J. F. Nicolas. 1995. Induction of homologous recombination in mammalian chromosomes by using the I-Sce I system of *Saccharomyces cerevisia*. Mol. Cel. Biol. 15:1968–1973.

5. Chu, T.-H. T., and R. Dornburg. 1995. Retroviral vector particles displaying the antigen-binding site of an antibody enable cell-type-specific gene transfer. J. Virol. 69:2659–2663.

6. Church, G. M., and W. Gilbert. 1984. Genomic sequencing. Proc. Natl. Acad. Sci. USA 81:1991–1995.

7. Eychene, A., C. Bechade, M. Marx, D. Laugier, P. Dezelee, and G. Calothy. 1990. Molecular and biological properties of c-mil transducing retroviruses generated during passage of Rous-associated virus type 1 in chicken neuroretina cells. J Virol 64:231–8.

8. Felder, M. P., A. Eychene, J. V. Barnier, I. Calogeraki, G. Calothy, and M. Marx. 1991. Common mechanism of retrovirus activation and transduction of c-mil and c-Rmil in chicken neuroretina cells infected with Rous-associated virus type 1. J Virol 65:3633–40.

9. Feuer, G., M. Taketo, R. C. Hanecak, and H. Fan. 1989. Two blocks in Moloney murine leukemia virus expression in undifferentiated F9 embryonal carcinoma cells as determined by transient expression assays. J. Virol. 63:2317–2324.

10. Flanagan, J. R., K. G. Becker, D. L. Ennist, S. L. Gleason, P. H. Driggers, B. Z. Levi, E. Appella, and K. Ozato. 1992. Cloning of a negative transcription factor that binds to upstream conserved region of Moloney murine leukemia virus. Mol. Cell Biol. 12:38–44.

11. Gama Sosa, M. A., D. H. Rosas, R. DcGasperi, E. Morita, M. R. Hutchinson, and R. Ruprecht. 1994. Negative regulation of the 5' long terminal repeat (LTR) by the 3' LTR in the murine proviral genome. Mol. Cel. Biol. 68:2662–2670.

12. Graham, F. L., and A. J. van der Eb. 1973. A new technique for the assay of infectivity of human adenovirus 5 DNA. Virology 52:456–467.

13. Gu, H., Y. R. Zou, and K. Rajewsky. 1993. Independent control of immunoglobin switch recombination at individual switch regions evidenced through Cre-loxP-mediated gene targeting. Cell. 73:1155–1164.

14. Hanley, T., and J. P. Merlie. 1991. Transgene detection in unpurified mouse tail DNA by polymerase chain reaction. BioTechnics. 10:56.

15. Hantzopoulos, P. A., B. A. Sullenger, G. Ungers, and E. Gilboa. 1989. Improved gene expression upon transfer of the adenosine deaminase minigene outside the transcriptional unit of a retroviral vector. Proc. Natl. Acad. Sci. USA 86:3519–3523.

16. Hoeben, R. C., A. A. Migchielsen, d. J. R. van, O. H. van, and d. E. A. van. 1991. Inactivation of the Moloney murine leukemia virus long terminal repeat in murine fibroblast cell lines is associated with methylation and dependent on its chromosomal position. J Virol 65:904–12.

17. Joyner, A. L. 1991. Gene targeting and gene trap screens using embryonic stem cells: New approaches to mammalian development. BioEssays 13:649–656.

18. Kasahara, N., A. M. Dozy, and Y. W. Kan. 1994. Tissus-specific targeting of retroviral vectors through ligand-receptor interactions. Science 266:1373–1376.

19. Kilby, N. J., M. R. Snaith, and J. A. H. Murray. 1993. Site-specific recombinases: tools for genome engineering. Reviews 9:413–421.

20. Linney, E., B. Davis, J. Overhauser, E. Chao, and H. Fan. 1984. Non-function of Moloney murine leukaemia virus regulatory sequence in F9 embryonal carcinoma cells. Proc. Natl. Acad. Sci. USA 84:3748–3752.

21. Lochet, M., M. Aboud, and R. M. Flugel. 1993. Increase in the basal transcriptional activity of the human foamy virus internal promoter by the homolgous long terminal repeat promoter in cis. NAR 21:4226–4230.

22. Loh, T. P., L. L. Sievert, and R. W. Scott. 1988. Negative regulation of retrovirus expression in embryonal carcinoma cells mediated by an intragenic domain. J. Virol. 62:4086–4095.

23. Loll, T. P., L. L. Sievert, and R. W. Scott. 1990. Evidence for a stem cell-specific repressor of moloney murine leukemia virus expression in embryonal carcinoma cells. Mol. Cell. Biol. 10:4045–4057.

24. Loh, T. P., L. L. Sivert, and R. W. Scott. 1987. Proviral sequences that restrict retroviral expression in mouse embryonal carcinoma cells. Mol. Cell. Biol. 7:3775–3784.

25. Mann, R., R. C. Mulligan, and D. Baltimore. 1983. Construction of a retrovirus packaging mutant and its use to produce helper-free defective retrovirus. Cell. 33:153–160.

26. Mansour, S. L., K. R. Thomas, and C. M.R. 1988. Disruption of the proto-oncogene int-2 in mouse embryo-derived stem cells: a general strategy for targeting mutations to non-selectable genes. Nature 336:348–352.

27. Miller, A. D., D. R. Trauber, and C. Buttimore. 1986. Factors involved in the production of helper virus-free retrovirus vector. Somatic Cell. Mol. Genet. 12:175–183.

28. Morgan, R. A., L. Couture, O. Elroy-Stein, J. Ragheb, B. Moss, and W. F. Anderson. 1992. Retroviral vectors containing putative internal ribosome entry sites: developement of a polycistronic gene transfer and applications to human gene therapy. N.A.R 20:1293–1299.

29. Nicolas, J. F., and C. Bonnerot. 1993. Répression et activation des rétrovirus murins dans les cellules totipotentes. Médecine/Sciences 9:191–197.

30. Nicolas, J. F., and J. Rubenstein. 1987. Retroviral vectors, p. 493–512. In E. Biotechnology series—Julian E. Davies (ed.), Vectors : A survey of molecular cloning vectors and their uses. Butterworths, Boston London Durban Singapore Sydney Toronto Wellington.

31. Pear, W. S., G. P. Nolan, M. L. Scott, and D. Baltimore. 1993. Production of high-titer helper-free retroviruses by transient transfection. Proc. Natl. Acad. Sci. USA. 90:8392–8396.

32. Peters, G., A. E. Lee, and C. Dickson. 1986. Concerted activation of two potential proto-oncogenes in carcinomas induced by mouse mammary tumour virus. Nature 320:628–631.

33. Petersen, R., G. Kempler, and E. Barklis. 1991. A stem cell-specific silencer in the primer-binding site of a retrovirus. Mol. Cel. Biol. 11:1214–1221.

34. Pulsinelli, G. A., and H. M. Temin. 1991. Characterization of large deletions occurring during a single round of retrovirus vector replication: novel deletion mechanism involving errors in strand transfer. J. Virol. 65:4786–4797.

35. Reddy, S., J. V. DeGregori, H. Von Melchner, and H. E. Ruley. 1991. Retrovirus promoter-trap vector to induce LacZ gene fusions in mammalian cells. J. Virol. 65:1507–1515.

36. Reddy, S., H. Rayburn, V. M. H., and R. H. E. 1992. Fluorescence-activated sorting of totipotent embryonic stem cells expressing developmentally regulated lacZ fusion genes. Proc. Natl. Acad. Sci. 89:6721–6725.

37. Rubenstein, J., J. F. Nicolas, and F. Jacob. 1984. Construction of a retrovirus capable of transducing and 38. Sanes, J., J. Rubenstein, and J. F. Nicolas. 1986. Use of a recombinant retrovirus to study post-implantation cell lineage in mouse embryos. EMBO J. 5:3133–3142.

39. Sauer, B. 1987. Functional expression of the cre-lox site-specific recombination system in the yeast *Saccharomyces cerevisia*. Mol. Cel. Biol. 7:2087–2096.

40. Sauer, B., and N. Henderson. 1988. Site-specific DNA recombination in mammalian cells by the Cre recombinase of bacteriophage P1. Proc. Natl. Acad. Sci. USA 85:5166–5170.

41. Savatier, N., D. Rocancourt, C. Bonnerot, and J.-F. Nicolas. 1989. A novel system for screening antiretroviral agents. J. Virol. 26:229–236.

42. Shafer, G. E., D. W. Emery, K. Gustafsson, S. Germana, W. F. Anderson, D. H. Sachs, and C. LeGuern. 1991. Expression of a swine class II gene in murine bone marrow hematopietic cells by retroviral mediated gene transfer. Proc. Natl. Acad. Sci. USA 88:9760–9764.

43. Sternberg, N., B. Sauer, R. Hoess, and K. Abremski. 1986. Bacteriophage P1 cre gene and its regulatory region. Evdence for multiple promoter and for regulation by DNA methylation. J. Mol. Biol. 187:197–212.

44. Stevenson, M., S. Haggerty, C. A. Lamonica, C. M. Meier, S. K. Welch, and A. J. Wasiak. 1990. Integration is not necessary for expression of human immunodeficiency virus type I protein products. J. Virol. 64:2421–2425.

45. Stuhlmann, H., and P. Berg. 1992. Homologous recombination of copakaged retrovirus RNAs during revers transcription. J. Virol. 66:2378–2388.

46. Swanstrom, R., R. C. Parker, H. E. Varmus, and J. M. Bishop. 1983. Transduction of a cellular oncogene: the genesis of Rous sarcoma virus. Proc. Natl. Acad. Sci. USA 80:2519–2523.

47. Takeuchi, Y., G. Simpson, R. G. Vile, R. A. Weiss, and M. K. Collins. 1992. Retroviral pseudotypes produced by rescue of a Moloney murin leukemia virus vector by C-type, but not D-type, retrovirus. Virology 186:792–794.

48. Tramblay, P. J., C. A. Kozak, and P. Jolicoeur. 1992. Identification of a novel gene, Vin-1, in murine leukemia virus-induced T-cell leukemias by provirus insertional mutagenesis. J. Virol. 66:1344–1353.

49. Trusko, S. P., E. K. Hoffman, and D. L. George. 1989. Transcriptional activation of cKi-ras proto-oncogene resulting from retroviral promoter insertion. N.A.R. 17:9259–9265.

50. Varela-Echavarria, A., C. M. Prorock, Y. Ron, and J. P. Dougherty. 1993. High rate of genetic rearrangement during replication of Moloney murin leukemia virus-based vector. J. Virol. 67:6357–6364.

51. von Melchner, H., and H. E. Ruley. 1989. Identification of cellular promoters by using a retrovirus promoter trap. J. Virol. 63:3227–3233.

52. Weiss, R., N. Teich, H. Varmus, and J. Coffin. 1985. RNA tumor viruses., p. 1222. (ed.), Molecular Biology of tumor viruses. Cold Spring Habor Laboratory., 53. Yee, Y. K., J. C. Moores, D. J. Jolly, J. A. Wolff, J. G. Respess, and T. Friedmann. 1987. Gene expression from transcriptionally disabled retroviral vectors. Proc. Natl. Acad. Sci. USA 84:5197–5201.

What is claimed is:

1. A retroviral vector comprising a nucleic acid molecule comprising:
    (A) retroelements that comprise a recombinant provirus when a target cell is infected by a retrovirus containing said retroelements;
    (B) a nucleotide sequence of interest, which can be expressed in the target cell and which can be transferred with said retroelements into the target cell and integrated into the recombinant provirus; and
    (C) a recognition sequence for the elimination of proviral sequences in the recombinant provirus, which are not necessary for expression of the nucleotide sequence of interest in the target cell after integration of the recombinant provirus into the target cell;
    wherein the vector is a defective Moloney murine leukemia provirus comprising said recognition sequence in a U3 region of its 3' LTR, a U5 region of its 5' LTR, or an R region of said provirus.

2. A cell having integrated into its genome a proviral structure comprising a single LTR sequence of a retroviral vector as claimed in claim 1, said LTR sequence comprising a unique copy of the nucleotide sequence of interest.

3. The cell as claimed in claim 2, which is a eukaryotic cell having a proviral structure that is free of PBS sequences, encapsidation and dimerization signals, and PPT.

4. A method for introducing a gene into a cell, wherein the method comprises infecting said cell in vitro with a retroviral vector as claimed in claim 1.

5. A method for expressing a molecule in a cell, wherein the method comprises:
    (A) providing a cell infected with a retrovirus as claimed in claim 1; and
    (B) culturing said cell under conditions permitting the expression of the nucleotide sequence of interest to thereby produce said molecule.

6. The method as claimed in claim 5, wherein the desired molecule is a polypeptide or RNA.

7. The method as claimed in claim 5, wherein the desired molecule is a protein encoded by the nucleotide sequence of interest.

8. A composition comprising a retroviral vector as claimed in claim 1 in combination with a pharmaceutically acceptable excipient.

9. A nucleic acid molecule comprising:
    (A) retroelements that comprise a recombinant provirus when a target cell is infected by a retrovirus containing said retroelements;
    (B) a nucleotide sequence of interest, which can be expressed in the target cell and which can be transferred with said retroelements into the target cell and integrated into the recombinant provirus; and
    (C) a recognition sequence for the elimination of proviral sequences in the recombinant provirus, which are not necessary for expression of the nucleotide sequence of interest in the target cell after integration of the recombinant provirus into the target cell, wherein the recognition sequence is recognized by a recombinase and wherein said recognition sequences are positioned downstream or upstream from the nucleotide sequence of interest;

wherein said retroelements comprise a 3' LTR or a 5' LTR region and the nucleotide sequence of interest is incorporated into the 3' LTR or 5' LTR region;

wherein the retroelements further comprise a U3 region of a 3' LTR, a U5 region of a 5' LTR, and an R region, and the nucleotide sequence of interest is incorporated into one of said regions; and further wherein said nucleic acid molecule comprises a nucleotide sequence coding for a recombinase that recognizes said recognition sequence.

10. The nucleic acid molecule as claimed in claim 9, wherein the retroelements comprise 5' LTR and 3' LTR regions and the nucleotide sequence coding for the recombinase is situated between the 5' LTR and 3' LTR regions.

11. The nucleic acid molecule as claimed in claim 9, wherein the recognition sequence, which can be recognized by a recombinase, is situated upstream from the nucleotide sequence of interest.

12. The nucleic acid molecule as claimed in claim 9, wherein the nucleotide sequence coding for the recombinase encodes CRE protein; and wherein the recognition sequence comprises two LoxP recognition sites after infection.

13. The nucleic acid molecule as claimed in claim 9, wherein the nucleotide sequence coding for the recombinase encodes CRE protein; and wherein the recognition sequence comprises two LoxP recognition sites after infection.

14. A retroviral vector comprising a nucleic acid molecule as claimed in claim 13.

15. The retroviral vector as claimed in claim 14, wherein the vector is a defective Moloney murine leukemia provirus comprising said recognition sequence in a U3 region of its 3' LTR, a U5 region of its 5' LTR, or an R region of said provirus.

16. A cell having integrated into its genome a proviral structure comprising a single LTR sequence of a retroviral vector as claimed in claim 14 or 15, said LTR sequence comprising a unique copy of the nucleotide sequence of interest.

17. The cell as claimed in claim 16, which is a eukaryotic cell having a proviral structure that is essentially free of PBS sequences, encapsidation and dimerization signals, and PPT.

18. A method for introducing a gene into a cell, wherein the method comprises infecting said cell in vitro with a retroviral vector as claimed in claim 14 or 15.

19. A method for expressing a desired molecule in a cell, wherein the method comprises:

(A) providing a cell infected with a retrovirus as claimed in claim 14 or 15; and (B) culturing said cell under conditions permitting the expression of the nucleotide sequence of interest to thereby produce said desired molecule.

20. The method as claimed in claim 19, wherein the desired molecule is a polypeptide or RNA.

21. The method as claimed in claim 19, wherein the desired molecule is a protein encoded by the nucleotide sequence of interest.

22. A composition comprising a retroviral vector as claimed in claim 14 or 15 in combination with a pharmaceutically acceptable excipient.

\* \* \* \* \*